United States Patent
Zarges et al.

(10) Patent No.: US 9,701,632 B2
(45) Date of Patent: Jul. 11, 2017

(54) PROCESS FOR THE PRODUCTION OF PHTHALIMIDES

(71) Applicant: LANXESS Deutschland GmbH, Cologne (DE)

(72) Inventors: Wolfgang Zarges, Cologne (DE); Georg Martin, Langenfeld (DE); Uwe Boeger, Leverkusen (DE); Michael Pies, Duisburg (DE); Guido Issling, Langenfeld (DE); Markus Koschorreck, Duesseldorf (DE)

(73) Assignee: LANXESS DEUTSCHLAND GMBH, Cologne (DE)

( * ) Notice: Subject to any disclaimer, the term of this patent is extended or adjusted under 35 U.S.C. 154(b) by 0 days.

(21) Appl. No.: 15/102,077

(22) PCT Filed: Dec. 19, 2014

(86) PCT No.: PCT/EP2014/078770
§ 371 (c)(1),
(2) Date: Jun. 6, 2016

(87) PCT Pub. No.: WO2015/091965
PCT Pub. Date: Jun. 25, 2015

(65) Prior Publication Data
US 2016/0304454 A1    Oct. 20, 2016

(30) Foreign Application Priority Data
Dec. 19, 2013  (EP) .................... 13198359

(51) Int. Cl.
*C07D 209/48*   (2006.01)
(52) U.S. Cl.
CPC ................. *C07D 209/48* (2013.01)
(58) Field of Classification Search
CPC .................................................. C07D 209/48
See application file for complete search history.

(56) References Cited

U.S. PATENT DOCUMENTS

| | | | |
|---|---|---|---|
| 1,968,253 A | 7/1934 | Jaeger | |
| 3,819,648 A | 6/1974 | Boehme | |
| 4,001,273 A | 1/1977 | Hetzel et al. | |
| 4,952,608 A | 8/1990 | Klipper et al. | |
| 6,649,663 B1 | 11/2003 | Klipper et al. | |
| 7,053,129 B1 * | 5/2006 | Klipper | B01J 39/04 521/32 |
| 2003/0144278 A1 | 7/2003 | Riedl et al. | |

FOREIGN PATENT DOCUMENTS

DE    2334379 A1    1/1975

OTHER PUBLICATIONS

M.C. Sze et al. "Hydrocarbon Processing, Make aromatic nitriles this way", 55, 1976, No. 2, p. 103.
M. Kuhara, "Concerning Phthalimide", Am. Chem. J., 3, 29, 1881, John Hopkins University, p. 26-30.
Faigl, B., "Application of organometallic methods for synthesis of carbon-14-labeled pesticide intermediates"., XP002724637, retrieved from STN Database accession No. 2010:309774.
Faigl, B., "Application of organometallic methods for synthesis of carbon-14-labeled pesticide intermediates", 115 (3-4), 123-128, CODEn: MKFKaI: ISSN: 1418-9933, 2009, XP008169466.
International Search Report from co-pending Application PCT/EP2014/078770 dated Apr. 8, 2015, 2 pages.

* cited by examiner

*Primary Examiner* — Shawquia Jackson

(57) ABSTRACT

The invention relates to a process to produce phthalimides by heating diammonium phthalate in the presence of aromatic solvents and to a process to produce phthalimides by heating diammonium phthalate in the presence of aromatic solvents for their recycled use during the ion exchanger production process. The diammonium phthalate is prepared by making use of the phthalic add salts solution resulted from the on exchanger production process.

17 Claims, No Drawings

PROCESS FOR THE PRODUCTION OF PHTHALIMIDES

The invention relates to a process to produce phthalimides by heating diammonium phthalate in the presence of aromatic solvents and to a process to produce phthalimides by heating diammonium phthalate in the presence of aromatic solvents for their recycled use during the ion exchanger production process. The diammonium phthalate is prepared by making use of the phthalic acid salts solution resulted from the ion exchanger production process.

Phthalimide and its derivatives are important intermediates in synthetic organic chemistry. Uses are, for example, found in the preparation of bio-active compounds i.e. antibacterial, analgesic, antifungal, plant growth regulator and also in dye industry. A further use is the introduction oaf phthalimide and derivatives thereof in crosslinked bead polymers to prepare specific ion exchangers and chelate resins.

Especially, U.S. Pat. No. 7,053,129 B1 discloses the use of phthalimide and its derivatives in the preparation process of a monodisperse ion exchangers having chelating functional groups. The ion exchangers preparation process comprises (a) reacting monomer droplets made from monovinylaromatic compounds and polyvinylaromatic compounds, and optional porogens and/or initiators, (b) amidomethylating the resultant monodisperse, crosslinked bead polymers with phthalimide derivatives, (c) converting the amidomethylated bead polymer to aminomethylated bead polymers, and (d) alkylating the aminomethylated bead polymers.

The elimination of the phthalic acid residue, and with this the release of the aminomethyl group, takes place in process step (c) via treatment of the phthalimidomethylated crosslinked bead polymer with aqueous or alcoholic solutions of an alkali metal hydroxide, such as, sodium hydroxide or potassium hydroxide.

During the ion exchanger preparation process, a large amount of solution containing salts of phthalic acid is resulted. Therefore, it would be reasonable to provide a process for the preparation of phthalimide starting with solution of salts of phthalic acid which can be returned into the preparation process of ion exchangers.

Various processes are known for preparing phthalimide. For example, phthalimide is usually prepared by the reaction of molten phthalic anhydride with ammonia. DE 2,334,379 describes such a process with elevated reaction temperature from 235° C. to 300° C. in the tubular reactor. This process cannot be applied in a process starting with phthalic add or its salts since further steps for the preparation of phthalic anhydride are required which makes the process cost intensive, uneconomically and unecologically.

U.S. Pat. No. 3,819,648 describes another production method for phthalimide based on a reaction between phthalic anhydride and urea with or without liquid aromatic solvents.

M. C. Sze et al. (Hydrocarbon Process. 55, 1976, No. 2, 103) describes that the ammonoxidation of o-xylene in the gas phase with ammonia under the condition of using metal oxide catalyst is another process to produce phthalimide, with phthalamide or phthalonitril as byproduct. However, such procedures with difficulty of removing the catalyst and achieving a product in higher purity are not suitable for the manufacture of phthalimide in large commercial scale.

Moreover, Kuhara et al. (Am. Chem. J. 3, 29, 1881) reports that phthalimide can be prepared by a two-step process a) by the preparation of monoammonium phthalate by heating diammonium phthalate and b) by isolating the monoammonium phthalate and further heating to prepare phthalimide. CA 1,031,351 discloses that the reaction of phthalic anhydride and ammonia batchwise gives a crude phthalimide which in general contains some amount of monoammonium phthalate and diammonium phthalate, besides ammonia, phthalic anhydride, phthalic acid and phthalimide. Due to the very little yield of phthalimide, this crude product is then washed by a melt of pure phthalimide or technical phthalimide at a temperature up to 260° C. to give a final 62% yield of phthalimide. Both processes are common that only reduced yields can be achieved and that these processes are therefore not usable in the preparation of phthalimide from phthalic acid or its salts.

Therefore, the known processes have the disadvantages that only low yields can be achieved and that they are therefore uneconomical or/and that further steps have to be performed and that they are ecologically disadvantaged.

There was consequently the need to provide a process which is suitable for the efficient preparation of phthalimide and which overcomes the disadvantage of the existing processes.

Surprisingly, it has now been found that phthalimide and its derivatives can be easily produced in high yields by heating diammonium phthalate and its derivatives in the presence of aromatic solvents.

Therefore, the present invention relates to a process for the preparation of compounds of formula (I)

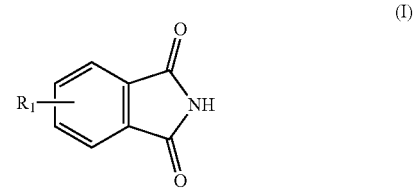

where $R_1$ is H, $C_1$-$C_4$-alkyl, $C_1$-$C_4$-alkoxy, $C_2$-$C_4$-alkenyl, benzyl, phenyl, phenylethyl, phenylpropyl, phenylbutyl. $R_1$ is preferred $C_1$-$C_4$-alkyl and H. $R_1$ is most preferred H. wherein compounds of formula (II) are heated at a temperature higher than 130° C.

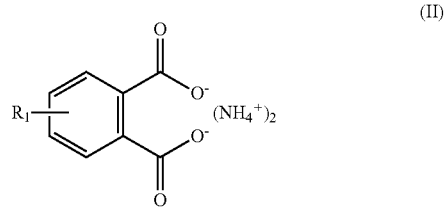

in the presence of an aromatic solvent or mixtures thereof.

Within the context of the invention, $C_1$-$C_4$-alkyl or $C_1$-$C_4$-alkoxy is a straight-chain, cyclic, branched or unbranched $C_1$-$C_4$-alkyl or $C_1$-$C_4$-alkoxy radical having 1 to 4 carbon atoms.

By way of example and preferably, $C_1$-$C_4$-alkyl is methyl, ethyl, n-propyl, isopropyl, n-, iso, s- or t-butyl, cyclopropyl, cyclobutyl and $C_1$-$C_4$-alkoxy is methoxy, ethoxy, n-propoxy, isopropoxy, t-butoxy, $C_1$-$C_4$-Alkyl is most preferred methyl or ethyl.

Within the context of the invention, $C_2$-$C_4$-alkenyl is preferred vinyl, allyl and butenyl.

Within the context of the invention phenylpropyl is phenyl-n-propyl and phenyl-s-propyl, preferably phenylpropyl is phenyl-n-propyl. Within the context of the invention phenylbutyl is phenyl-n-butyl, phenyl-s-butyl and phenyl-iso-butyl.

The scope of the invention encompasses all radical definitions, parameters and illustrations above and listed hereinbelow, specified in general or within areas of preference, in any combination with one another, i.e. also between the particular areas and areas of preference. The definition w. % means in the context of the invention % by weight.

Suitable aromatic solvents or mixtures are, for example, those from the group consisting of monocyclic and bicyclic aromatic hydrocarbons containing 6 to 18 carbon atoms. By way of example and preferably, aromatic solvents are n-butylbenzene, 1-methylnaphthalene, 2-methylnaphthalene, diisopropylnaphthalene, di-tertiary-butylnaphthalene, alpha-naphthyl methyl ether, halobenzene more preferred dichlorobenzene and 1,2,4-trichlorobenzene, 1,2,3,4-tetrahydronaphthalin, mixtures of these solvents. Most preferred aromatic solvent is 1,2-dichlorobenzene.

In a further embodiment of the invention aromatic solvents are, for example, those from the group consisting of monocyclic and bicyclic aromatic hydrocarbons containing 6 to 18 carbon atoms and which has a boiling point higher than 130° C. and builds an azeotrop with water. Preferably aromatic solvents are those from the group consisting of monocyclic and bicyclic aromatic hydrocarbons containing 6 to 18 carbon atoms and which has a boiling point higher than 130° C. and builds an azeotrop with water.

In a further embodiment of the invention the aromatic solvent is one in which at least 30 w. % of the compounds of the formula (I) are solved at a temperature of at least 20° C. below the boiling point of the aromatic solvent and in which compounds of formula (I) at room temperature are solved only up to 5 w. %.

The transition from compound of formula (II) to compound of formula (I) is normally carried out at a temperature over 130° C. Preferably the transition from compound of formula (II) to compound of formula (I) is carried out at a temperature between 145° C. and 190° C.

Compound of formula (II) can be initially dissolved, for example, in water and brought into contact with the aromatic solvents. Preferably, the compound of formula (II) is initially dissolved in water and then brought into contact with the aromatic solvent. Preferably, compound of formula (II) is preheated before it is brought into contact with the aromatic solvent. The most preferable preheating temperature is between 70° C. and 80° C. The addition of compound of formula (II) to the aromatic solvents can take place, for example, in portions, semicontinuously or continuously. The addition of compound of formula (II) to the aromatic solvent takes place preferably continuously. The addition of compound of formula (II) to the aromatic solvent can be performed at every temperature but normally at a temperature by which the solvents are liquid. Preferably the addition of compound of formula (II) to the aromatic solvent is performed at a temperature over 130° C. but particularly preferably at a temperature between 140° C. and 200° C. and most preferably between 145° C. and 190° C. After the completion of adding compound of formula (II) to the aromatic solvent, the temperature can be increased up to the boiling point of the reaction mixture. Preferably after the completion of adding compound of formula (II) to the aromatic solvent the temperature is increased up to the boiling point of the reaction mixture. Since the compound of formula (II) is often solved in water before it is added to the aromatic solvents, the resulting aromatic medium can contain up to 50 w. % of water, preferably up to 30 w. % water. Generally and preferably it is advised to remove the water by azeotropic distillation during the preparation process of compound of formula (I). Generally, after the water is removed the temperature can be increased up to the boiling point of the aromatic solvent. Preferably, after the water is removed the temperature is increased up to the boiling point of the aromatic solvent. Preferably, the temperature increase can be carried out slowly.

In one preferred embodiment, the aromatic solvent is heated up to 30° C. below the boiling points. The compound of the formula (II) is then added continuously into the suitable aromatic solvent. The reaction is preferably performed by heating up to 30° C. below the boiling points and the water is removed by azeotropic distillation during the preparation process. After the water is removed the temperature is increased up to the boiling point of the aromatic solvent.

The work-up can take place in a manner known for a person skilled in the art.

Often in industrial process by the production of primary amine groups, for example in the well-known Gabriel synthesis of primary amine, salts of phthalic acid are resulted during the hydrolysis of the alkylated amide. These salts or the acid can be converted to phthalimide in the same reaction sequence as described.

Within the context of the invention, during the industrial production of the ion exchanger, salts of phthalic acid is resulted in ion exchanger production. A further embodiment of our invention is related to a process for recovering of compounds of formula (I) from a process wherein such compounds have to be used to insert primary amine groups in chemical compounds wherein (a) converting a phthalic acid salt solution, preferably obtainable by the preparation of aminomethylated ion exchange resins, by acid hydrolyzing to a phthalic acid, (b) preparing compound of formula (II) by reacting the phthalic acid with ammonia water, (c) preparing compound of formula (I) by heating compound of formula (II) in the presence of aromatic solvent at a temperature higher than 130° C.

By way of example and preferably, the phthalic acid salts solution according to our invention was prepared according to following patents (U.S. Pat. No. 4,952,608 A, U.S. Pat. No. 6,849,663 B1, U.S. Pat. No. 7,053,129 B), the contents of which are incorporated into the present application in relation to the following steps (a) reacting monomer droplet made from at least one monovinylaromatic compound including styrene and at least one polyvinylaromatic compound to give a cross-linked bead polymer, Preferred monovinylaromatic compounds for this step are monoethylenically unsaturated compounds, such as, styrene, vinyltoluene, ethylstyrene, α-methylstyrene, chlorostyrene, chloromethylstyrene, alkyl acrylates, and alkyl methacrylates. Particular preference is given to the use of styrene or mixtures of styrene with the above-mentioned monomers.

Preferred polyvinylaromatic compounds for this step are multifunctional ethylenically unsaturated compounds, such as, divinylbenzene, divinyltoluene, trivinylbenzene, divinylnaphthalene, trivinylnaphthalene, 1,7-octadiene, 1,5-hexadiene, ethylene glycol dimethacrylate, trimethylolpropane trimethacrylate, or allyl methacrylate.

(b) amidomethylating the crosslinked bead polymer from step (a) with compounds of formula (I). In this step, the preferred compound of formula (I), phthalimide or methylphthalimide, is dissolved in a solvent and mixed with formalin to be used as the amidomethylating agent. The bead polymer is condensed with the compounds of formula (I) in the presence of catalyst which comprises oleum, sulfuric add or sulfur trioxide, (c) converting the amidomethylated bead polymer from step (b) to an aminomethylated bead polymer, (d) dividing the remaining phthalic add salt solution from the aminomethylated on exchangers.

The elimination of the phthalic add residue, and with this the release of the aminomethyl group, preferably takes place in process step (c) via treatment of the phthalimidomethylated crosslinked bead polymer with aqueous or alcoholic solutions of an alkali metal hydroxide, at temperatures of from 100 to 250° C.

The amonimethylated bead polymer can be converted by reaction with further agents, as for example 2-chloromethylpiridyne, to anionic or cationic exchangers but the aminomethylated bead polymer can also be used as ion exchangers without further modifications.

The phthalic acid salts solution preferably used according to our invention is, by example and preferably an aqueous solution, in particular, disodium phthalate solution resulted from the ion exchanger preparation. This solution is generally mixed with waste water solutions resulted from different industrial preparation processes. The amount of the disodium phthalate in this solution is normally in the range of 10 w. %-30 w. %. preferably 15 w. % -25 w. %. To efficiently make good use of the phthalic add salts solution during the ion exchanger preparation, a process of starting from this solution to prepare compounds of the formula (I) and later on recycling the obtained compounds of formula (I) into the ion exchanger production is a further embodiment of our invention.

Starting from the phthalic acid salts solution, acid is used to hydrolyze them to phthalic acid, Preferably the phthalic add salts solution is a water solution. For example and preferably, acids for the converting of phthalic acid salts solution to phthalic acid are being selected from the group consisting of perchloric acid, hydrochloric acid, sulfuric acid, nitric acid, nitrous acid, phosphoric acid, hydrofluoric add. Preferred add for the hydrolyzing process of the phthalic add salts is sulfuric acid.

According to the invention, add and phthalic add salts solution are preferably added batchwise. The reaction has to be carried out by heating. Normally the reaction is carried out by a temperature between 20° C. to 95° C., preferably at a temperature between 80° C. and 95° C. Most preferably the reaction is carried out at a temperature between 90° C. and 95° C.

In general the preparation of the phthalic acid is performed by a) bringing in contact the phthalic acid salt solution with the respective acid and b) heating the reaction mixture and c) cooling the reaction mixture down and d) filter and obtain phthalic acid crystals. Just as the heating of the phthalic acid salt solution can also be performed during step a) of the preparation method. Furthermore, generally for a skilled person known work-up methods can be performed for the purification or preparation of the crystalline phthalic add.

Generally and preferable the phthalic add crystalline is firstly brought into contact with solvents under stirring to form an uniform mixture. The most preferable solvent is water. According to the invention, by example and preferably, ammonia water, is added into this mixture. Generally the amount of ammonia in the ammonia water is between 15 w. % to 30 w. %, preferably the amount of ammonia in the ammonia water is between 15 w. % to 25 w. %. The reaction can take place under heating, preferably between 50° C. to 95° C., most preferably the temperature for the reaction to prepare compound of the formula (II) is between 60 and 75° C. Generally, to prevent diammonium phthalate, optionally, or its derivatives, from crystallization, the reaction solution of compound of formula (II) is stored at a heated status, preferably at a temperature higher than 50° C.

Generally and preferably, the solution of compounds of formula (II) is then brought into contact with the aromatic solvents in a process as disclosed above to be converted to compound of formula (I). This compound of formula (I) can then be employed again in a process to insert primary amine groups in ion exchangers.

In the manner according to the invention, it is possible to prepare the compounds of he formula (I) in high yields in industrial processes.

The compounds of the formula (I) prepared according to the invention are suitable as intermediates e.g. for the production of fine chemicals, medicament and agrochemicals, and particularly suitable for their recycled application in the on exchanger preparation according to the invention.

EXAMPLES

Example 1

Step 1: Acid Hydrolyzing to Phthalic Acid 318 g water is added into a 2-liter multi-neck flask equipped with stirrer and thermometer and heated to 95° C. At this temperature, 1.524 g disodium phthalate water (19.6%) and 301.8 g sulfuric acid are added simultaneously into the flask within 1 hour. Then the mixture is stirred at 95° C. for 1 hour and then cooled down to 20° C.

The phthalic acid is crystallized and vacuumed up at 20° C. with suction filter. Then 215 g water is used to wash phthalic acid.

Step 2: Phthalic Acid to Diammonium Phthalate

The freshly washed phthalic acid in the suction filter is mixed with 89 g water under stirring to form an uniform mixture. 221 g 20% ammonia water is added into the mixture within 1 hour at 70° C. Then 545 g 47% diammonium phthalate solution (a theoretical yield based on 90% conversion of disodium phthalate) is produced. To prevent diammonium phthalate from crystallization, the solution is stored at a temperature higher than 55° C.

Step 3: Diammonium Phthalate to Phthalimide 450 g (345 ml) o-dichlorobenzene is placed into a 1-liter four-necked round-bottom flask and heated up to 150 to 155° C. At this temperature, 545 g diammonium phthalate water solution (47%) pre-heated at 70° C. is then added into this flask continuously within 4 hours, Water is directly distilled and separated from the system. During the process, part of diammonium phthalate is transferred to phthalmide, producing some ammonium and additional water which is also distilled. After the addition of diammonium phthalate solution is completed and no more water is distilled, the temperature inside the flask is increased slowly within 3 hours to make o-dichlorobenzene reflux. Water resulted from this process is further distilled away. The reaction is ended when the solution becomes clear. The reaction solution is then cooled down to the room temperature upon stirring. Phthalimide is crystallized, filtered, separated and then dried inside a vacuum drying oven.

The reaction gives 160 g phthalimide with a purity higher than 99%, in a yield of 85%.

What is claimed is:

1. A process for producing compounds of formula (I)

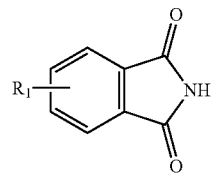

(I)

wherein $R_1$ is selected from the group consisting of H, $C_1$-$C_4$-alkyl, $C_1$-$C_4$-alkoxy, $C_2$-$C_4$-alkenyl, benzyl, phenyl, phenylethyl, phenylpropyl, and phenylbutyl, the process comprising heating compounds of formula (II)

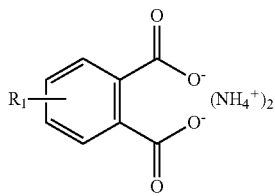

(II)

in the presence of an aromatic solvent at a temperature greater than 130° C.

2. The process according to claim 1, wherein the aromatic solvent comprises a solvent in which at least 30 w. % of the compounds of the formula (I) are solved at a temperature of at least 30° C. below the boiling point of the aromatic solvent, and in which compounds of formula (I) at room temperature are solved only up to 5 w. %.

3. The process according to claim 1, wherein the aromatic solvent builds an azeotrope with water.

4. The process according to claim 1, wherein the temperature is 145° C. to 190° C.

5. The process according to claim 1, wherein the compound of formula (II) is added to the aromatic solvent at a temperature within the range of 145° C. to 190° C. to produce a reaction mixture, and, after the completion of the adding, the temperature of the reaction mixture is increased up to the boiling point of the reaction mixture.

6. The process according to claim 1, wherein the aromatic solvent is selected from the group consisting of n-butylbenzene, 1-methylnaphthalene, 2-methylnaphthalene, diisopropylnaphthalene, di-tertiary-butylnaphthalene, alpha-naphthyl methyl ether, halobenzene, 1,2,3,4-tetrahydronaphthalin, and mixtures thereof.

7. The process according to claim 1, futher comprising removing water during the process by azeotropic distillation.

8. A process for recovering of compounds of formula (I)

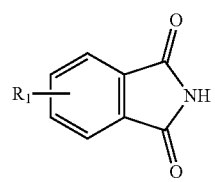

(I)

wherein $R_1$ is selected from the group consisting of H, $C_1$-$C_4$-alkyl, $C_1$-$C_4$-alkoxy, $C_2$-$C_4$-alkenyl, benzyl, phenyl, phenylethyl, phenylpropyl, and phenylbutyl from a process wherein the compounds of the formula (I) are used to insert primary amine groups in chemical compounds, the process comprising:

(a) converting a phthalic acid salt solution by acid hydrolyzing to a phthalic acid, (b) reacting the phthalic acid from step (a) with ammonia water to produce compounds of the formula (II)

$$\text{(II)}$$

and (c) converting the compounds of the formula (II) back into compounds of formula (I) according to the process of claim 1.

9. The process for recovering compounds of formula (I) according to claim 8, wherein the phthalic acid salt solution is prepared by:

(a1) reacting monomer droplets made from at least one monovinylaromatic compound including styrene and at least one polyvinylaromatic compound to give a crosslinked bead polymer, (b1) amidomethylating the crosslinked bead polymer from step (a) with the compound of the formula (I), (c1) converting the amidomethylated bead polymer from step (b) to an aminomethylated bead polymer, and (d1) dividing remaining phthalic acid salt solution from the aminomethylated bead polymer.

10. The process for recovering compounds of formula (I) according to claim 8, further comprising, in step (a), reacting the acid and phthalic acid salts solution at a temperature of 20° C. to 95° C.

11. The process for recovering compounds of formula (I) according to claim 8, further comprising, in step (b), reacting the phthalic acid with the ammonia water at a temperature of 50° C. to 95° C.

12. The process according to claim 1, further comprising dissolving the compounds of formula (II) in water prior to contacting the compounds of formula (II) with the aromatic solvent.

13. The process according to claim 12, further comprising, after dissolving the compounds of the formula (II) in water to form a solution, heating the solution to a temperature of 70° C. to 80° C., prior to contacting the compounds of formula (II) with the aromatic solvent.

14. The process according to claim 1, wherein:
$R_1$ is H or $C_1$-$C_4$-alkyl; and
the aromatic solvent is selected from the group consisting of monocyclic and bicyclic aromatic hydrocarbons containing 6 to 18 carbon atoms and having a boiling point higher than 130° C. and which builds an azeotrope with water.

15. The process according to claim 1, wherein:
$R_1$ is H, methyl or ethyl; and
the aromatic solvent is selected from the group consisting of n-butylbenzene, 1-methylnaphthelene, 2-methylnaphthalene, diisopropylnaphthalene, di-tertiary-butyl-naphthalene, alpha-naphthyl methyl ether, dichlorobenzene, 1,2,4-trichlorobenzene, 1,2,3,4-tetrahydronaphthalin, and mixtures thereof.

16. The process according to claim 1, wherein:

$R_1$ is H; and the aromatic solvent is dichlorobenzene.

17. The process according to claim 16, wherein the process comprises:

dissolving the compounds of the formula (II) in water to form a solution;

preheating the solution to a temperature of 70° C. to 80° C.;

heating the aromatic solvent to a temperature at most 30° C. below its boiling point;

adding the preheated solution to the heated solvent to produce a reaction mixture;

heating the reaction mixture to a temperature at most 30° C. below its boiling point;

azeotropically distilling off water from the reaction mixture;

after removing the water, increasing the temperature of the reaction mixture to its boiling point, and produce compounds of the formula (I) in product solution;

cooling the product solution to crystalize the compounds of the formula (I); and separating the crystalized compounds of the formula (I) from the product solution.

\* \* \* \* \*